US009670168B2

(12) United States Patent
Bragg et al.

(10) Patent No.: US 9,670,168 B2
(45) Date of Patent: *Jun. 6, 2017

(54) FACILE METHOD FOR PREPARATION OF 5-NITROTETRAZOLATES USING A FLOW SYSTEM

(71) Applicant: Pacific Scientific Energetic Materials Company, Chandler, AZ (US)

(72) Inventors: Jon G. Bragg, Phoenix, AZ (US); John W. Fronabarger, Sun Lakes, AZ (US); Michael D. Williams, Gilbert, AZ (US)

(73) Assignee: Pacific Scientific Energetic Materials Company, Chandler, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/160,998

(22) Filed: Jan. 22, 2014

(65) Prior Publication Data

US 2014/0206885 A1 Jul. 24, 2014

Related U.S. Application Data

(60) Provisional application No. 61/755,167, filed on Jan. 22, 2013.

(51) Int. Cl.
*C07D 257/04* (2006.01)
*C07D 257/06* (2006.01)
*C07D 403/12* (2006.01)
*A01N 47/38* (2006.01)
*C06B 43/00* (2006.01)

(52) U.S. Cl.
CPC ................ *C07D 257/06* (2013.01)

(58) Field of Classification Search
CPC .. C07D 257/04; C07D 257/06; C07D 403/12; A01N 47/38; C06B 43/00
USPC .......................... 548/251; 422/198
See application file for complete search history.

(56) References Cited

U.S. PATENT DOCUMENTS

| 2,066,954 | A | 1/1937 | von Herz |
| 3,054,800 | A | 9/1962 | Burchfield et al. |
| 3,111,524 | A | 11/1963 | Wiley et al. |
| 4,093,623 | A | 6/1978 | Gilligan et al. |
| 4,094,879 | A | 6/1978 | Bates et al. |
| 4,552,598 | A | 11/1985 | Lee et al. |
| 6,375,871 | B1 | 4/2002 | Bentsen et al. |
| 6,437,104 | B1 | 8/2002 | Nickel et al. |
| 6,469,147 | B2 | 10/2002 | Nickel et al. |
| 6,495,016 | B1 | 12/2002 | Nawracala |
| 6,648,015 | B1 | 11/2003 | Chow et al. |
| 6,737,026 | B1 | 5/2004 | Bergh et al. |
| 7,253,288 | B2 | 8/2007 | Renz et al. |
| 2007/0161801 | A1 | 7/2007 | Renz et al. |
| 2015/0361057 | A1 | 12/2015 | Bottaro et al. |

FOREIGN PATENT DOCUMENTS

| WO | 0159013 | 8/2001 | |
| WO | 03037502 | 5/2003 | |
| WO | WO 2006029193 A2 * | 3/2006 | ........... C07D 257/04 |
| WO | 2014116654 | 7/2014 | |

OTHER PUBLICATIONS

Lowe, H., R.D. Axinte, D. Breuch, C. Hofmann, J.H.Petersen, R. Pommersheim, and A. Wang "Flow chemistry: Imidazole-based ionic liquid syntheses in micro-scale" Chemical Engineering Journal 2010, 163 (3), pp. 429-437.*
Lowe, H., R.D.Axinte, D. Breuch, C. Hofmann, J.H.Petersen, R. Pommersheim, and A. Wang "Flow chemistry: Imidazole-based ionic liquid syntheses in micro-scale" Chemical Engineering Journal 2010, 163 (3), pp. 429-437.*
Gutmann, B., J. Roduit, D. Roberge, and C. Kappe "Synthesis of 5-Substituted 1H-Tetrazoles from Nitriles and Hydrazoic Acid by Using a Safe and Scalable High-Temperature Microreactor Approach" Angew. Chem. Int. Ed. 2010, 49: pp. 7101-7105.*
C. Galli, "Substituent Effects on the Sandmeyer reaction. Quantitative Evidence for Rate-determining Electron Transfer" J. Chem. Soc. Perkin Trans. II, 1984, pp. 897-902.
Lowe, et al. 'Flow chemistry: Imidazole-based ionic liquid syntheses in micro-scale', Chemical Engineering Journal, 2010, vol. 163, No. 3, pp. 429-437.
PCT/US2014/012472, International Search Report and Written Opinion dated May 2, 2014, 10 pages.
Fortt et al., Continuous-Flow Generation of Anhydrous Diazonium Species, Organic Process Research & Development, 2003, 762-768, vol. 7, No. 5.
Wootton et al., On-Chip Generation and Reaction of Unstable Intermediates, Lab-On-A-Chip, 2002, 4, 5-7.
Doyle et al., Alkyl Nitrite-Metal Halide Deamination Reaction. 2. Substitutive Deamination of Arylamines by Alkyl Nitrites and Cooper (II) Halides. A Direct and Remarkably Efficient Conversion of Arylamines to Aryl Halides, J. Org. Chem., 1977, 2426-2431, vol. 42, No. 14.
Tegrothenhuis et al., Normal gravity testing of a microchannel phase separator for resource utilization, NASA/CR-2001-210955 (Jun. 2001).
Brooks et al., Component development for a microchannel in situ propellant production system, 2002, AIChE 2002 Spring National Meeting held Mar. 10-14, 2002 in New Orleans, Louisiana.
Ahn et al., Centrifugal gas-liquid separation under low-gravity conditions, Separation and Purification Technology, 2000, 121-129, vol. 19, No. 1.
Gunther et al., Transport and reaction in microscale segmented gas-liquid flow, Lab-On-A-Chip, 2004, 4, 278-286.
Amon et al., Direct Methanol Micro Fuel Cell for Powering Micro Sensors, http://www.darpa.mil/mto/mpg/summaries/2003.sub.--1/cmu.html (2003).
Kralj et al., Preparation of Sodium Nitrotetrazolate Using Microreactor Technology, American Institute of Aeronautics and Astronautics, 41.sup.st AIAA/ASME/SAE/ASEE Joint Propulsion Conference and Exhibit, Jul. 10-13, 2005, Tuscan, AZ.

(Continued)

*Primary Examiner* — Alicia L Otton
*Assistant Examiner* — Sagar Patel
(74) *Attorney, Agent, or Firm* — Kilpatrick Townsend & Stockton LLP

(57) ABSTRACT

Described are methods for preparing salts of 5-nitrotetrazolate that include reacting aqueous solutions of 5-aminotetrazole, an acid, and sodium nitrite in a continuous flow system at an elevated temperature.

19 Claims, 3 Drawing Sheets

(56) References Cited

OTHER PUBLICATIONS

International Patent Application No. PCT/US2014/012472, International Preliminary Report on Patentability dated Aug. 6, 2015.
Dimian, Alexandre C., et al., Integrated Design and Simulation of Chemical Processes, Chemical-Aided Chemical Engineering, 35, $2^{nd}$ Edition, 2014, 12 pages, Elsevier B.V.
U.S. Appl. No. 15/000,444, filed Jan. 19, 2016, Bragg et al.
U.S. Appl. No. 14/731,613, Non-Final Office Action dated Mar. 11, 2016.
Klapoetke et al., Z Anorg. Allg. Chem., 2013, 639, (5), 681-688 (Published Online: Mar. 15, 2013).
International Patent Application No. PCT/US2016/013858, Search Report and Written Opinion dated Apr. 6, 2016.
Europe Patent Application No. 14743596.0, Extended European Search Report dated May 10, 2016.

\* cited by examiner

FACILE METHOD FOR PREPARATION OF 5-NITROTETRAZOLATES USING A FLOW SYSTEM

CROSS REFERENCE TO RELATED APPLICATIONS

This application is related to and claims priority benefits from U.S. Provisional Application Ser. No. 61/755,167 ("the '167 application"), filed on Jan. 22, 2013, entitled FACILE METHOD FOR PREPARATION OF 5-NITROTETRAZOLATES USING A FLOW SYSTEM. The '167 application is hereby incorporated in its entirety by this reference.

FIELD OF THE INVENTION

The present invention is directed to the field of substituted tetrazole synthesis and manufacture. More particularly, the present invention is directed to processes for preparing substituted tetrazoles and tetrazolate salts, such as sodium 5-nitrotetrazolate, utilizing small scale and/or flow techniques. The use of the present technique results in less hazardous and more efficient manufacturing processes.

BACKGROUND

Sodium 5-nitrotetrazolate ("NaNT," 6) has found application as both a stand-alone energetic material and as a reactant or constituent in a variety of explosives and propellants. Typically, NaNT is synthesized via a Sandmeyer type reaction that involves displacement of a diazonium group by a nucleophile, in this case nitrite ion resulting in a nitro group, in the presence of cupric salts. C. Galli, "Substituent Effects on the Sandmeyer reaction. Quantitative Evidence for Rate-determining Electron Transfer" *J. Chem. Soc. Perkin Trans. II*, No. 5, 1984, pp. 897-902; U.S. Pat. No. 4,093,623. Energetics chemists have been utilizing this method for a number of years to produce NaNT in small batches.

This procedure, outlined in FIG. 1, involves addition of a solution of commercially available 5-aminotetrazole ("5-AT," 1) in aqueous nitric acid to a solution of copper (II) sulfate and sodium nitrite to generate the diazonium ion (3) which undergoes substitution to afford the acid copper salt of 5-nitrotetrazole ("5-NT," 5). During the addition of the 5-AT and nitric acid, the reaction temperature must be tightly controlled at or below 18° C. due to the thermal instability of the diazonium intermediate. The second process step utilizes aqueous sodium hydroxide to convert the acid copper salt of 5-NT into NaNT and generates copper oxide as a byproduct.

This method is problematic, particularly during larger scale procedures, due to "micro-detonations" which occur if the mixing of the 5-AT and sodium nitrite solutions is not tightly controlled. These micro-detonations may be caused by nitrogen oxide fumes from the reaction solution reacting with droplets of 5-AT on surfaces in the reactor to form 5-diazotetrazole (4) which may spontaneously detonate in solution when the concentration exceeds 1%.

These micro-detonations may be strong enough to break glass and may result in release of the potentially explosive reaction mixture. It was determined that inclusion of a small amount of $CuSO_4$ to the 5-AT solution prior to addition to the $CuSO_4$-nitrite solution was effective in preventing the micro-detonations by catalyzing conversion of 5-diazotetrazole, in the presence of nitrite, to 5-NT. Use of these cupric salts, however, add additional steps (and cost and/or time) to the procedure, which result in lower overall reaction yields. These additional operations include two manual filtration steps in which operators are exposed to considerable quantities of $CuH(5-NT)_3$ and NaNT, both of which are explosives. In considering this process, it is quite clear that a less hazardous, alternate procedure is needed for large scale laboratory production of NaNT.

As opposed to the processes described in U.S. Pat. Nos. 3,054,800, and 3,111,524, this invention provides a simple, continuous flow process for the synthesis of 5-nitrotetrazolates starting from 5-AT and which convert it directly, via a moderately high temperature Sandmeyer reaction, to a salt of 5-nitrotetrazolate without the use of copper.

U.S. Pat. No. 7,253,288 to R. N. Renz, M. D. Williams, and J. W. Fronabarger, also describes an alternate method for producing NaNT utilizing microreactor technology, which does not use copper to stabilize the tetrazole diazonium intermediate and involves direct reaction of 5-AT/nitric acid with sodium nitrite at ambient temperature and in a continuous flow regime. Unlike a batch process, this procedure generates only very small amounts of the unstable reaction intermediates in a dilute media, and they are subsequently consumed via substitution as a part of the flow process. This process provides a safe method for preparation of 5-nitrotetrazolates, as only minor amounts of the intermediates are generated per unit time and accumulation is not possible, but requires extensive time and an appropriate microreactor system optimized for 5-NT production for the flow process.

The methods for preparation of 5-nitrotetrazolate salts outlined above may be prohibitive either in terms of time and safety for the batch process or for possessing an appropriate microreactor system optimized for 5-NT production for the flow process. There is a need to improve the efficiency and safety of the chemical process by providing a method for preparation of 5-nitrotetrazolate salts, specifically NaNT, quickly from 5-AT and utilizing a method in which all of the unstable intermediates are immediately and fully consumed.

SUMMARY OF THE INVENTION

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

According to certain embodiments of the invention, a method for preparing salts of 5-nitrotetrazolate comprises reacting aqueous solutions of 5-aminotetrazole, an acid, and sodium nitrite in a continuous flow system at an elevated temperature, which in some embodiments may be in a range of approximately 50° C. to 100° C., or may be in a range of approximately 70° C. to 90° C.

In certain embodiments, the 5-aminotetrazole and the acid comprise one reactant stream, and the sodium nitrite comprises a second reactant stream. The acid may comprise nitric acid, sulfuric acid, or perchloric acid.

The continuous flow system may further comprise a heated zone that is held at the elevated temperature. The heated zone may comprise a preheat zone for each reactant stream, a mixing zone that combines the first reactant stream and the second reactant stream into a reactant mixture, and a reaction zone that is configured to retain the reactant mixture in the heated zone until the reaction is complete. In some embodiments, the reaction zone retains the reactant mixture in the heated zone until a product with at least 50% yield of NaNT is achieved.

According to additional embodiments of the invention, a continuous flow system for preparing salts of 5-nitrotetrazolate comprises a first reactant stream comprising 5-aminotetrazole and an acid, and a second reactant stream comprising sodium nitrite, a mixing zone that combines the first reactant stream and the second reactant stream into a reactant mixture, and a reaction zone that is configured to retain the reactant mixture at an elevated temperature until the reaction is complete. The acid may comprise nitric acid, sulfuric acid, or perchloric acid.

The preheat zone, the mixing zone, and the reaction zone may be held at the elevated temperature in a range of approximately 50° C. to 100° C., or may be held in a range of approximately 70° C. to 90° C. In some embodiments, each reactant stream passes through a preheat zone prior to entering the mixing zone. The reaction zone may retain the reactant mixture until a product with at least 50% yield of NaNT is achieved.

In some embodiments, reaction product of 5-aminotetrazole, a nitrite salt, a suitable acid, and water is prepared via a continuous flow process at an elevated temperature.

According to certain other embodiments, a method for preparing a salt of 5-nitrotetrazolate comprises (a) mixing an aqueous solution of 5-aminotetrazole and an acid with an aqueous solution of a nitrite salt in a continuous flow system to form a reactant mixture, (b) retaining the reactant mixture in a heated zone of the continuous flow system at an elevated temperature, (c) forming an aqueous product within the heated zone, and (d) collecting and cooling the aqueous product. The acid may comprise nitric acid, sulfuric acid, or perchloric acid. In some embodiments, the acid is nitric acid, and the nitrite salt is sodium nitrite. In some embodiments, the elevated temperature may be in a range of approximately 50° C. to 100° C., or may be in a range of approximately 70° C. to 90° C.

DETAILED DESCRIPTION

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

According to certain embodiments, a procedure has been developed which provides facile access to high purity NaNT by combining the reactants at an elevated temperature. Under appropriate conditions, the diazonium formation and substitution occur at such a rapid rate that there is no opportunity for buildup of hazardous intermediates.

An advantage of the present method is that copper (II) is not required for intermediate stabilization and so there is no need for isolation or separation of byproducts. In addition, the process provides a high purity, concentrated aqueous solution of NaNT, which may be directly utilized in subsequent reactions or cooled to induce crystallization and isolated as an end product.

Figure 1:
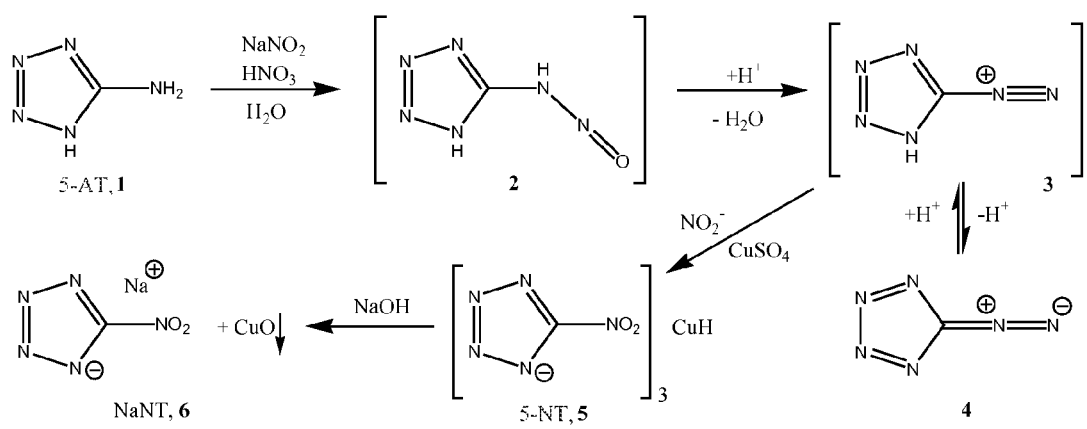
FIG. 1 is a depiction of a method used for preparation of NaNT, according to certain embodiments of the present invention.
Figure 2:
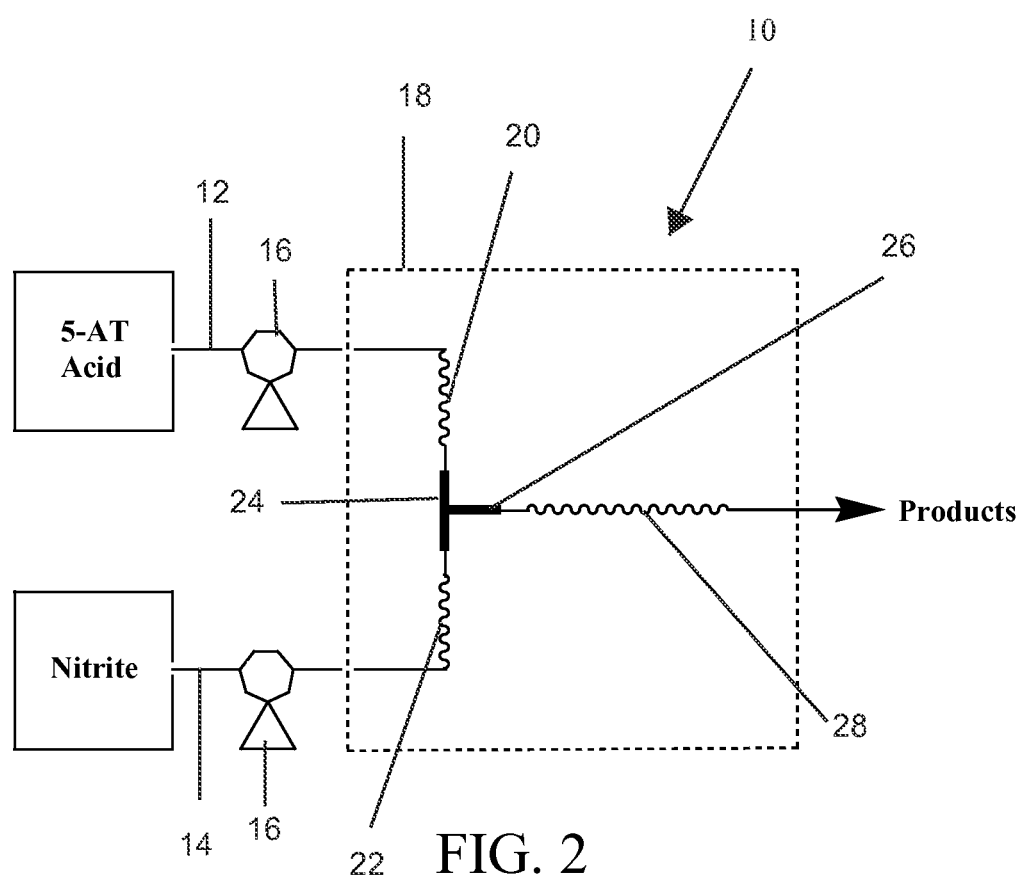
FIG. 2 is a flow diagram of a method used for preparation of NaNT, according to certain embodiments of the present invention.
Figure 3:
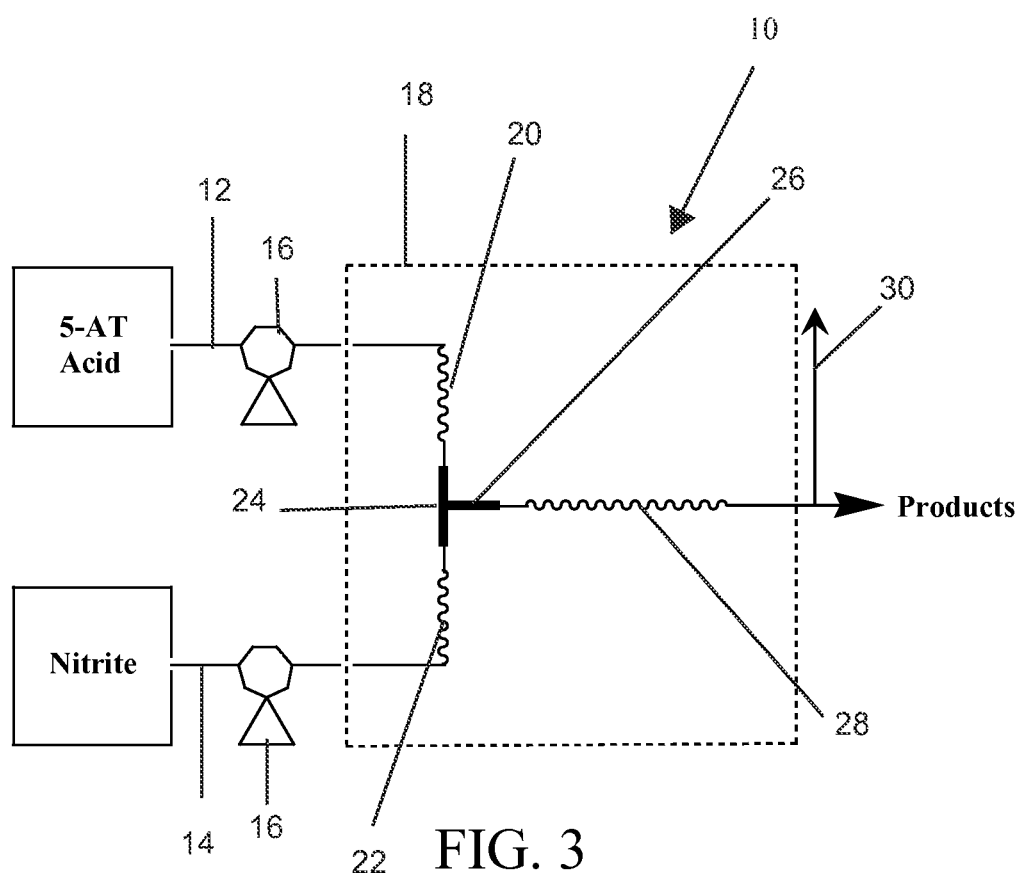
FIG. 3 is a flow diagram of a method used for preparation of NaNT, according to certain embodiments of the present invention.

According to certain embodiments of the present invention, NaNT is prepared utilizing a continuous flow system 10, such as the embodiments illustrated in FIGS. 2 and 3.

In these embodiments, NaNT may be prepared by reacting aqueous solutions of 5-AT, a suitable acid such as nitric, sulfuric or perchloric acid, and sodium nitrite in the continuous flow system 10. The components may be reacted under conditions suitable to synthesize NaNT.

In certain embodiments, as illustrated in FIGS. 2 and 3, the components may be introduced into the continuous flow system 10 by mixing water, 5-AT, and an appropriate acid to form a first reactant stream 12, and adding aqueous solution of an appropriate nitrite as a second reactant stream 14. In other embodiments, each reactant may be separately introduced into the continuous flow system 10.

The acid may be selected from any known acid or mixture of acids that will, when mixed with 5-AT and a nitrite, facilitate the substitution of the tetrazole. Most strong inorganic acids are suitable for use in the present invention. Non-limiting examples would include nitric, sulfuric, or perchloric acids. Similarly, the nitrite may be selected from any known nitrite or mixture of nitrites that will, when mixed with 5-AT and an acid, facilitate the substitution of the tetrazole. Non-limiting examples would include sodium, potassium, or lithium nitrites.

The reactants may be supplied to the continuous flow system 10 in amounts that are sufficient to effect the desired substitution reaction to provide a 5-nitrotetrazolate. The nitrite may be supplied to the continuous flow system 10 in an amount sufficient to react with the acid to generate a diazonium intermediate from the 5-AT and provide sufficient excess nitrite to form 5-nitrotetrazolate. Alternatively, the nitrite may be supplied to the continuous flow system 10 in a molar ratio of at least two moles of nitrite per mole of 5-AT. Similarly, the acid may be supplied to the continuous flow system 10 in an amount sufficient to react with the nitrite to generate a diazonium intermediate from the 5-AT and provide a 5-nitrotetrazolate. Alternatively, the acid may be supplied to the continuous flow system 10 in a molar ratio of at least one mole of acid per mole of 5-AT.

In certain embodiments, one or more pumps 16 may be used to transport the reactant steams 12, 14 from storage tanks or vessels into the continuous flow system 10.

Downstream of the pumps 16, the reactant streams 12, 14 may separately enter a heated zone 18. As illustrated in FIGS. 2 and 3, the heated zone 18 may comprise one or more preheat zones 20, 22, a mixing zone 24, and/or a reaction zone 28. In some embodiments, the preheat zones 20, 22 may not be necessary if the reactant streams 12, 14 enter the heated zone 18 at a temperature that is suitable for completion of the reaction. The heated zone 18 may be designed so that reaction may be carried out at any temperature that allows for and/or facilitates rapid completion of the substitution reaction. Alternatively, the reaction may be carried out in the heated zone 18 with an elevated temperature in a range of approximately 50° C. to 100° C. Alternatively, the reaction may be performed in the heated zone 18 with an elevated temperature in a range of approximately 70° C. to 90° C.

In certain embodiments, all of the components of the heated zone 18 may be heated by a common heat source, such as a common water bath, oven, heat exchanger, or other heat source. In other embodiments, different heat sources may be used among the various preheat zones 20, 22, mixing zone 24, and reaction zone 28 as needed and/or desired to achieve different temperatures within each area in order to further optimize the reaction within the continuous flow system 10.

For example, the first reactant stream 12 may pass through the preheat zone 20 and the second reactant stream 14 may pass through a preheat zone 22 prior to being combined in the mixing zone 24. In certain embodiments, the preheat zones 20, 22 may comprise a pair of preheating coils.

Once the reactant streams 12, 14 have passed through the preheat zones 20, 22, the reactant streams 12, 14 are introduced into the mixing zone 24, where the reactant streams 12, 14 are mixed to form a reactant mixture 26. According to certain embodiments, the mixing zone 24 may be a mixing T. It is contemplated that mixing of the reactants may be performed using any type of single device that would allow continuous blending or merging of the reactant streams 12, 14 including but not limited to a transfer pump, a static mixer, an oscillatory baffled reactor, a mechanical agitator, and/or a continuously stirred tank reactor. Alternatively, it is contemplated that a series of mixing devices could be used to introduce the reactants gradually via a manifold.

The reactant mixture 26 then passes from the mixing zone 24 into the reaction zone 28. According to certain embodiments, the reaction zone 28 may comprise a reaction coil of sufficient length and volume to provide a retention time in the heated zone 18 until the reaction is complete. More specifically, the reaction zone 28 is configured to allow the reaction to proceed within the heated zone 18 until a product with at least 50% yield of NaNT is achieved.

Upon mixing, the combination of reactants generates large volumes of gas as a result of substitution of the diazonium species. As illustrated in FIG. 3, this gas may optionally be released using a gas/liquid separator 30 either inside or outside the heated zone 18 or, as illustrated in FIG. 2, may be confined in the flow tubing until it exits the flow reactor. The products then exit the heated zone 18 and are collected in a suitable vessel.

The manufacturing process depicted in FIGS. 2 and 3 may be carried out, either in whole or in part, in a microfluidic flow system. It is understood that the flow system may be comprised of tubing of a composition suitable for containing the reactants at the prescribed temperatures. Additionally, the tubing shall be of any diameter that allows for flow rates and retention times that provide for the rapid conversion of 5-AT to a 5-nitrotetrazolate. Similarly, it is understood that the pumping devices 16 will supply the reactants at a flow rate that allows for continuous mixing as well as a system retention time that allows for complete reaction in the heated zone 18.

It has been found that the application of the processes described herein achieves the goals of providing a process for rapid preparation of 5-nitrotetrazolates, specifically NaNT, that is both safe and more efficient than conventional processes and may be suitable for use in large scale manufacturing operations.

Those skilled in the art will appreciate that the specifics of the processes provided may be modified, without departing from the present disclosure.

EXAMPLES

The following examples demonstrate the utility of the present processes.

Example 1

5-AT (88 g, 1.03 mol) was dissolved in 1 L of aqueous 1.2M nitric acid (73 mL of 16.4 mmol/mL)—reactant stream 12. Sodium nitrite (159 g, 2.3 mol) was dissolved in 1 L of deionized water—reactant stream 14. The reactant streams 12, 14 were pumped at a rate of 3 mL/minute through the preheat columns 20, 22 and into the mixing T 24. The tubing diameter was 0.076 inches (ID). The length of the tubing from the pumps 16 into the mixing T 24 was 2.5 feet and was 50 feet after the mixing T 24. This configuration provided a retention time of ~0.37 minutes in the heated zone 18 and a post mixing volume of ~44.5 mL. The heated zone 18 (in this case a water bath) was maintained at 70-72° C. during operation. The continuous flow system 10 was allowed to come to equilibrium for ~22.5 minutes before product was acquired.

After the product exited the heated zone 18, it was allowed to cool to ambient temperature in an e-flask. Analysis (HPLC or FTIR) of the reaction mixture indicated sodium 5-nitrotetrazolate with >50% yield.

Example 2

5-aminotetrazole monohydrate (121 g, 1.17 mol) was dissolved in 1 L of aqueous 1.3M sulfuric acid (65 mL of 17.6 mmol/mL)—reactant stream 12. Sodium nitrite (284 g, 4.12 mol) was dissolved in 1 L of deionized water—reactant stream 14. The reactant streams 12, 14 were pumped at a rate of 1 mL/minute through the preheat columns 20, 22 and into the mixing T 24. The tubing diameter was 0.076 inches (ID). The length of the tubing from the pumps 16 into the mixing T 24 was 2.5 feet and was 50 feet after the mixing T 24. This configuration provided a retention time of ~1.11 minutes in the heated zone 18 and a post mixing volume of ~44.5 mL. The heated zone 18 (in this case a water bath) was maintained at 70-72° C. during operation. The flow reactor was allowed to come to equilibrium for ~30 minutes prior to product collection.

After the product exited the heated zone 18, it was allowed to cool to ambient temperature in an e-flask. Analysis (HPLC or FTIR) of the reaction mixture indicated sodium 5-nitrotetrazolate with >50% yield.

Note: When utilizing sulfuric acid, additional nitrite salt is required during the reaction due to generation of nitrosylsulfuric acid, part of which may be lost as NOx.

Different arrangements of the components depicted in the drawings or described above, as well as components and steps not shown or described are possible. Similarly, some That which is claimed is:

1. A method for preparing sodium salts of 5-nitrotetrazolate in a continuous flow system comprising a mixing T followed by a reaction coil, the method comprising
   mixing aqueous solutions of 5-aminotetrazole, an acid, and sodium nitrite in the mixing T to form a reactant mixture; and
   reacting the reactant mixture in the reaction coil at an elevated temperature at or above 50° C.;
   wherein the mixing T and the reaction coil comprise a cross-sectional diameter of at least 0.076 inches (ID) and are not located on a microfluidic reactor chip.

2. The method of claim 1, wherein the acid comprises nitric acid, sulfuric acid, or perchloric acid.

3. The method of claim 1, wherein the 5-aminotetrazole and the acid comprise one reactant stream, and the sodium nitrite comprises a second reactant stream.

4. The method of claim 3, wherein the continuous flow system further comprises a preheat zone for each reactant stream.

5. The method of claim 4, wherein the reaction coil retains the reactant mixture in the reaction coil until a product with at least 50% yield of NaNT is achieved.

6. The method of claim 1, wherein the elevated temperature is in a range of 50° C. to 100° C.

7. The method of claim 1, wherein the elevated temperature is in a range of approximately 70° C. to 90° C.

8. A continuous flow system for preparing sodium salts of 5-nitrotetrazolate comprising:
   a first reactant stream comprising 5-aminotetrazole and an acid, and a second reactant stream comprising sodium nitrite;
   a mixing T that combines the first reactant stream and the second reactant stream into a reactant mixture; and
   a reaction coil that is configured to retain the reactant mixture at an elevated temperature at or above 50° C. until the reaction is complete;
   wherein each reactant stream has a flow rate of at least 1 mL/min; and
   wherein the mixing T and reaction coil are not located on a microfluidic reactor chip.

9. The continuous flow system of claim 8, wherein the acid comprises nitric acid, sulfuric acid, or perchloric acid.

10. The continuous flow system of claim 8, wherein each reactant stream passes through a preheat zone prior to entering the mixing T.

11. The continuous flow system of claim 10, wherein the preheat zone, the mixing T, and the reaction coil are held at the elevated temperature in a range of 50° C. to 100° C.

12. The continuous flow system of claim 10, wherein the preheat zone, the mixing T, and the reaction coil are held at the elevated temperature in a range of approximately 70° C. to 90° C.

13. The continuous flow system of claim 8, wherein the reaction coil retains the reactant mixture until a product with at least 50% yield of NaNT is achieved.

14. A method for preparing a sodium salt of 5-nitrotetrazolate in a continuous flow system comprising a mixing T followed by a reaction zone, the method comprising
   (a) mixing an aqueous solution of 5-aminotetrazole and an acid with an aqueous solution of sodium nitrite the mixing T to form a reactant mixture;
   (b) retaining the reactant mixture in the reaction zone at an elevated temperature at or above 50° C.;
   (c) forming an aqueous product within the reaction zone; and
   (d) collecting and cooling the aqueous product;
   (e) wherein the mixing T comprises a cross-sectional diameter of at least 0.076 inches (ID), and the mixing T is not located on a microfluidic reactor chip.

15. The method of claim 14, wherein the acid comprises nitric acid, sulfuric acid, or perchloric acid.

16. The method of claim 14, wherein the acid is nitric acid.

17. The method of claim 14, wherein the elevated temperature is in a range of approximately 50° C. to 100° C.

18. The method of claim 14, wherein the elevated temperature is in a range of approximately 70° C. to 90° C.

19. The method of claim 8, wherein each reactant stream has a flow rate of at least 3 mL/min.

* * * * *